United States Patent [19]

Drake

[11] 4,200,586

[45] Apr. 29, 1980

[54] INHIBITING THE CARBON-CARBON DOUBLE BOND ISOMERIZATION OF SUBSTITUTED OR UNSUBSTITUTED HYDROCARBON COMPOUNDS

[75] Inventor: Charles A. Drake, Nowata, Okla.

[73] Assignee: Phillips Petroleum Company, Bartlesville, Okla.

[21] Appl. No.: 868,370

[22] Filed: Jan. 10, 1978

[51] Int. Cl.$^2$ .................. C07C 121/30; C07C 121/48; C07C 121/70
[52] U.S. Cl. .............................. 260/464; 260/465 K; 260/465.8 R; 260/465.9; 260/593 R; 260/601 R; 560/205; 562/598; 568/840; 568/581; 585/3
[58] Field of Search ...................... 260/465.9, 465.8 R, 260/464, 601 R, 593 P; 560/218; 562/600; 598/920

[56] References Cited

U.S. PATENT DOCUMENTS

| | | | |
|---|---|---|---|
| 2,960,490 | 11/1960 | Hinkes | 260/45.85 |
| 3,985,786 | 10/1976 | Drake | 260/465.8 R |
| 4,001,294 | 1/1977 | Drake et al. | 260/465.8 R |

OTHER PUBLICATIONS

Hine, Physical Organic Chemistry, 1956, pp. 22–23, McGraw-Hill, N.Y., N.Y.

*Primary Examiner*—Joseph Paul Brust

[57] ABSTRACT

The carbon-carbon double bond isomerization of a substituted or an unsubstituted hydrocarbon compound having olefinic unsaturation in a less stable form to an isomer of said compound having olefinic unsaturation in a more stable form is inhibited by contacting with said compound having the more unstable form with an alkali metal salt of a di-, tri- or tetracarboxylic acid.

29 Claims, No Drawings

INHIBITING THE CARBON-CARBON DOUBLE BOND ISOMERIZATION OF SUBSTITUTED OR UNSUBSTITUTED HYDROCARBON COMPOUNDS

BACKGROUND OF THE INVENTION

The invention relates to a method for inhibiting the carbon-carbon double bond isomerization of substituted or unsubstituted hydrocarbon compounds. In one aspect the invention relates to a method for inhibiting the carbon-carbon double bond isomerization of a mononitrile. In another aspect the invention relates to a process for producing unsaturated dinitriles employing the above-noted method for inhibiting the carbon-carbon double bond isomerization of a mononitrile.

Isomerization reactions involving the carbon-carbon double bond rearrangement of a variety of substituted or unsubstituted hydrocarbon compounds are well known in the art. Isomerization reactions are frequently employed in a process to increase the overall production of a specific compound from a multicomponent feedstream as, for example, in a process for producing 2-butene from a feedstream comprising 1-butene and 2-butene. However, there are other instances, as in the present invention, where it is desirable to inhibit an isomerization reaction. For example it is frequently desirable to store a certain compound having olefinic unsaturation in a less stable form as compared to an isomer of said compound having olefinic unsaturation in a more stable form; however, isomerization often occurs spontaneously, thus providing a mixture of isomers. Such a situation exists in the storage of 5-methyl-5-hexenenitrile, for example, of which a portion will spontaneously isomerize to produce 5-methyl-4-hexenenitrile, the more stable isomer. Likewise it is desirable to inhibit the isomerization of a compound existing in a less stable form when said compound is being used as a reactant in a reaction and an isomer of said compound having a more stable form produces an undesirable product. Such a situation can exist when an olefinically unsaturated mononitrile such as, for example, acrylonitrile, an olefinic hydrocarbon reactant such as, for example, isobutylene and the reaction product of the unsaturated mononitrile and the olefinic hydrocarbon reactant, frequently referred to as a monoadduct, such as, for example, 5-methyl-5-hexenenitrile, produced by reacting acrylonitrile and isobutylene, are reacted in the presence of an aqueous diluent to produce an olefinically unsaturated dinitrile product frequently referred to as a diadduct, such as, for example, 5-methylene-1,9-nonanedinitrile. This reaction is generally described in U.S. Pat. No. 3,985,786, issued to Charles A. Drake on Oct. 12, 1976. In the above-described reaction it is generally undesirable for the 5-methyl-5-hexenenitrile to isomerize to 5-methyl-4-hexenenitrile during the reaction. Inhibitors suitable for use in the above-described reaction are disclosed in U.S. Pat. No. 4,001,294, issued to Charles A. Drake et al on Jan. 4, 1977. As described therein as little as 0.5 weight percent of 5-methyl-4-hexenenitrile in the reaction mixture as described above will adversely affect the fiber-forming properties of polymers derived from the 5-methylene-1,9-nonanedinitrile diadduct produced by the reaction. Therefore it is clear that the use of inhibitors is of particular importance such as, for example, in the storage of certain compounds and in carrying out certain reactions, and although some such inhibitors are presently known and recognized in the art, there is still a need for additional inhibitors and inhibitors having improved inhibiting properties.

Accordingly, it is an object of the invention to inhibit the carbon-carbon double bond isomerization of a compound having olefinic unsaturation in a less stable form to a compound having olefinic unsaturation in a more stable form.

Another object of the invention is to inhibit the carbon-carbon double bond isomerization of a monoadduct produced by reacting an olefinic hydrocarbon and an olefinically unsaturated mononitrile when said monoadduct is reacted with a mononitrile to produce a dinitrile.

Another object of the invention is a carbon-carbon double bond isomerization inhibitor having little or no tendency to corrode equipment required in various processes employing said inhibitor.

Still another object of the invention is a carbon-carbon double bond isomerization inhibitor having little or no tendency to corrode equipment when employed in reactions in which an aqueous diluent is used.

Still another object of the invention is a carbon-carbon double bond isomerization inhibitor which is an effective inhibitor in concentrations substantially lower than the concentration generally required for prior art inhibitors.

These and other objects of the invention will be apparent to those skilled in the art upon studying the specification and the appended claims.

According to the invention an acyclic or an alicyclic substituted or unsubstituted hydrocarbon compound having 4 to 30 carbon atoms per molecule and having olefinic unsaturation in a less stable form is inhibited from isomerizing to produce a corresponding isomer having olefinic unsaturation in a more stable form by contacting the compound with an alkali metal salt of a di-, tri- or tetracarboxylic acid. The use of such alkali metal salts substantially precludes the carbon-carbon double bond isomerization of a wide variety of substituted and unsubstituted hydrocarbons even when employed in concentrations substantially lower than the concentrations generally required for prior art inhibitors.

Further according to the invention, the presence of an alkali metal salt of a di-, tri- or tetracarboxylic acid in a reaction mixture containing at least one olefinic hydrocarbon reactant, at least one olefinically unsaturated mononitrile reactant, at least one monoadduct reaction product of an olefinic hydrocarbon compound and an olefinically unsaturated mononitrile compound in the presence of an aqueous diluent substantially inhibits the carbon-carbon double bond isomerization of the above-described monoadduct from a less stable form with respect to the olefinic unsaturation to a more stable form. In addition it has been found that such salts are essentially noncorrosive with respect to the materials generally used in a reactor and associated equipment suitable for carrying out the above process.

DETAILED DESCRIPTION OF THE INVENTION

The isomerization inhibitor according to the instant invention is at least one alkali metal salt of a di-, tri- or tetracarboxylic acid represented by the general formula $MO_2C-R(CO_2Z)_n$ wherein n is an integer having a value of 1, 2 or 3; wherein M is selected from the group consisting of lithium, sodium, potassium, rubidium and cesium; wherein each Z is independently selected from the group consisting of hydrogen, lithium, sodium, potassium, rubidium and cesium; and wherein R is selected from the group consisting of a valence bond, a hydrocarbyl radical and a hydroxy substituted hydrocarbyl radical, each of the hydrocarbyl radical and the hydroxy substituted hydrocarbyl radical having from 1 to 8 carbon atoms and having a valence equal to n+1. A number of runs hereinafter described were carried out with potassium salt inhibitors, in particular potassium salts of aliphatic dicarboxylic acids. Examples of suitable potassium salts of aliphatic dicarboxylic acids include potassium oxalate, potassium malonate, potassium succinate, potassium glutarate, potassium adipate, potassium pimelate, potassium suberate, potassium azelate, potassium sebacate, potassium 2,3-dimethylbutanedioate, potassium 2-methylbutanedioate, potassium 2-methylpropanedioate, potassium 2-methylhexanedioate, potassium 2-ethyl-3-methylpentanedioate, potassium 3,3-dimethylpentanedioate, and potassium 2,3-diethylbutanedioate. Mixtures of any two or more of the above compounds can also be employed if desired.

Further examples of suitable alkali metal salt inhibitors within the scope of the invention include potassium hydrogen terephthalate, lithium hydrogen isophthalate, sodium hydrogen orthophthalate, potassium terephthalate, potassium isophthalate, sodium orthophthalate, sodium citrate, lithium oxalate, sodium oxalate, rubidium oxalate, cesium oxalate, sodium hydrogen oxalate, rubidium hydrogen oxalate, lithium malonate, sodium succinate, rubidium glutarate, cesium adipate, lithium pimelate, sodium suberate, rubidium azelate, cesium sebacate, lithium 2,3-dimethylbutanedioate, sodium 2-methylhexanedioate, rubidium 2-ethyl-2-methylpentanedioate, cesium 3,3-dimethylpentanedioate, lithium 2,3-diethylbutanedioate, sodium hydrogen adipate, potassium hydrogen pimelate, rubidium hydrogen suberate, cesium hydrogen azelate, lithium propane 1,2,3-tricarboxylate, potassium propane 1,2,3-tricarboxylate, potassium citrate, lithium citrate, sodium dihydrogen citrate, potassium dihydrogen citrate, sodium hydrogen citrate, potassium hydrogen citrate, sodium dihydrogen propane 1,2,3-tricarboxylate, potassium dihydrogen propane 1,2,3-tricarboxylate, sodium cyclopentane 1,2,3,4-tetracarboxylate, potassium cyclopentane 1,2,3,4-tetracarboxylate, cesium cyclopentane 1,2,3,4-tetracarboxylate, potassium trihydrogen cyclopentane 1,2,3,4-tetracarboxylate, potassium dihydrogen cyclopentane 1,2,3,4-tetracarboxylate, potassium hydrogen cyclopentane 1,2,3,4-tetracarboxylate and mixtures of any two or more such compounds, as well as mixtures of one or more of such compounds with one or more of the potassium salts of aliphatic dicarboxylic acids.

The isomerization inhibitor additives of the present invention are believed to be effective generally for inhibiting or retarding the carbon-carbon double bond isomerization of acyclic or alicyclic substituted or unsubstituted hydrocarbon compounds of 4-30 carbon atoms per molecule and having olefinic unsaturation in a less stable form to olefinic unsaturation in a more stable form. As used herein, the term "less stable form" refers to olefinic unsaturation having a lower degree of alkylation than the "more stable form" which, correspondingly, refers to olefinic unsaturation having a higher degree of alkylation. The effect of the degree of alkylation at the carbon-carbon double bond on olefin isomer stability is discussed, for example, on pages 22 and 23 of *Physical Organic Chemistry* by Jack Hine, McGraw-Hill Book Co., Inc., New York (1956).

By means of general formulas (I) and (II), the isomerization which is described above and which is inhibited or retarded by the additives of this invention can be illustrated as follows:

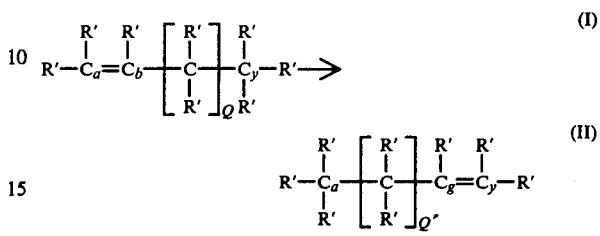

wherein each R' is independently selected from the group consisting of hydrogen, alkyl radicals of 1-10 carbon atoms, and substituted alkyl radicals (as defined below) of 1-10 carbon atoms and wherein the carbon atoms in the carbon-carbon double bond represented by $C_a=C_b$ in formula (I) have fewer alkyl or substituted alkyl radicals attached thereto as compared to the carbon atoms in the carbon-carbon double bond represented by $C_g=C_y$ in formula (II). Q and Q' are the same or different and are within the range of from 0 to 7. The subscript letters used to identify the carbon atoms in formulas (I) and (II) do not necesarily identify the same carbon atoms in both formulas, for example, $C_a$ in formula (I) is not necessarily $C_a$ in formula (II). A substituted alkyl radical as used herein is an alkyl radical in which at least one of the hydrogens of the alkyl radical is replaced with a substituent other than a hydrocarbyl radical. Such substituent can be selected from a wide variety of groups. Examples of such substituents include the following:

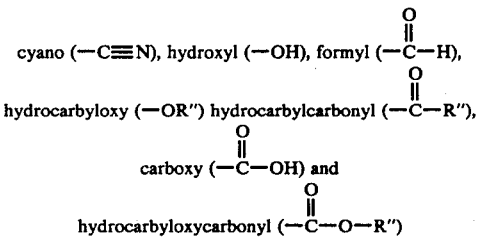

wherein R'' is a hydrocarbyl radical of 1–10 carbon atoms. Furthermore, said substituent should be attached to a carbon atom which is at least two carbon atoms (inclusive of the substituent-bearing atom) removed from the nearest carbon atom of the olefinic double bond in the compound of general formula (I). This latter proviso is intended to exclude from consideration those starting compounds wherein the substituent could have a significant effect on the relative stability of the isomers apart from the degree of alkylation of said olefinic double bonds by virtue of its closeness to the olefinic double bond.

With further reference to compounds of general formula (I), it is also within the scope of the instant invention that alkyl or substituted alkyl groups on carbon atoms a and y can be joined or combined to thus form a carbocyclic ring system incorporating carbon atoms a, b and y therein.

Examples of suitable starting compounds of general formula I whose olefinic isomerization can be effectively inhibited or retarded by the additives according to the instant invention include 1-butene, 1-pentene, 1-hexene, 1-octene, 1-triacontene, 3-methylcyclohexene, 3-ethylcyclooctene, 5-methyl-5-hexenenitrile, 5-hexenal, 5-hexenol, 6-methoxy-1-hexene, 6-decyloxy-1-hexene, 1-octen-7-one, 5-hexenoic acid, 3-methyl-4-cyclooctenecarboxylic acid, methyl 5-hexenoate, decyl 5-hexenoate, decyl 19-eicosenoate, 20-decyloxy-1-eicosene, 3-heptyl-5-cyano-8-decyloxycyclododecene, and mixtures of any two or more thereof.

It has also been found that the isomerization inhibitors of the present invention are particularly suitable for use in reactions involving the production of unsaturated nitriles, such as the reactions described in U.S. Pat. No. 3,985,786 noted above. In these reactions an olefinically unsaturated nitrile, an olefinic hydrocarbon and a monoadduct of an olefinic hydrocarbon and an olefinically unsaturated nitrile are reacted, preferably in the presence of water, to yield olefinically unsaturated dinitrile products having a greater number of carbon atoms than the unsaturated nitrile reactant.

Any unsaturated mononitrile can be employed in the practice of this invention to produce a dinitrile provided the mononitrile contains a cyano group attached to a carbon atom adjacent and doubly bonded to a carbon atom which is attached to at least one hydrogen atom. Preferably the mononitrile reactant is free of acetylenic unsaturation and contains from 1 to 2 nonconjugated olefinic carbon-carbon double bonds as the sole unsaturation, while the total number of carbon atoms in the mononitrile reactant is within the range of 3 to 18, more preferably within the range of 3 to 8. Illustrative unsaturated mononitrile reactants include those represented by the formula R'''CH=CR'''—CN wherein each R''' is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, for example alkylcycloalkyl, cycloalkylalkyl, aralkyl and arylcycloalkyl radicals. Examples of unsaturated nitriles meeting the requirements of the above formula are acrylonitrile, methacrylonitrile, 2-decenenitrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, and 5-p-tolyl-2-nonenenitrile and mixtures of any two or more thereof.

Any acyclic or cyclic olefinic hydrocarbon compound can be employed to produce a monoadduct which is in turn employed to produce a diadduct according to the invention, provided that the compound has at least one allylic hydrogen atom and the doubly bonded carbon atoms are free of cyano groups. The olefinic hydrocarbons preferably are free of acetylenic unsaturation and have from 3 to 18 carbon atoms per molecule with from 1 to 2 nonconjugated olefinic carbon-carbon double bonds as the sole unsaturation. The preferred types of these compounds are the open chain monoolefinic hydrocarbons represented by the formula $R^{IV}{}_2C=CR^{IV}-CHR^{IV}{}_2$, wherein each $R^{IV}$ is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the carbon-carbon double bond. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and mixtures of any two or more thereof.

Suitable monoadducts include any monoadduct reaction product of an olefinic hydrocarbon, as hereinabove defined, and an unsaturated mononitrile, as hereinabove defined. It is currently believed that the olefinic hydrocarbon compound and the unsaturated mononitrile react in accordance with the "ene" reaction to produce, as the principal monoadduct reaction product, a compound having the structural formula

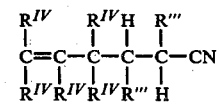

Generally, a lesser amount of an isomeric monoadduct reaction product having the formula

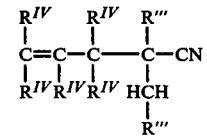

is also produced. $R'''$ and $R^{IV}$ are as defined above for the unsaturated mononitrile and the open chain monoolefinic hydrocarbon.

As used herein the "ene" reaction is the addition of a compound with a double bond (enophile) to an olefin possessing an allylic hydrogen (ene) and involves allylic shift of one double bond, transfer of the allylic hydrogen to the enophile and bonding between the two unsaturated termini.

Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2-(n-butyl)-4-pentenenitrile, 2-(n-butyl)-5-phenyl-4-pentenenitrile, and mixtures of any two or more thereof.

The diadduct reaction products, i.e. the dinitriles, obtained by the process of this invention comprise the reaction product mixtures formed by the monoaddition of an unsaturated mononitrile and any monoadduct reaction product. Exemplary of a diadduct reaction product is the reaction product mixture consisting of the major isomer species 5-methylenenonanedinitrile and 5-methyl-4-nonenedinitrile, and minor isomer species 2-methyl-4-methyleneoctanedinitrile, 2,4-dimethyl-4-octenedinitrile, 2,4-dimethyl-3-octenedinitrile, 2,6- dimethyl-4-methyleneheptanedinitrile and 2,4,6-trimethyl-3-heptenedinitrile.

The amount of inhibitor utilized according to the instant invention can be conveniently expressed in terms of the weight percent of inhibitor added based on the amount of less stable isomer. The amount of inhibitor employed can be selected over a rather wide range but will broadly be in the range of about 0.0001 to about 10% by weight; however, based upon the results of the runs described herein the amount of inhibitor employed will preferably be within a range of from about 0.0005 to about 2% by weight based on the less stable isomer. In the specific process under discussion the amount of inhibitor employed is based upon the weight of monoadduct reaction product described above.

In a continuous reaction process, the isomerization inhibitor of the instant invention is often conveniently added as a dispersion or solution of the inhibitor in water. In a batch process, which is less preferred, the charge order of reactants including the inhibitor dispersed or dissolved in water is not critical and any convenient charge order can be employed.

The effluent from the reaction zone in either a batch or continuous reaction process can be treated by conventional separation procedures and the aqueous phase separated and recycled as desired to the reaction zone. It will be readily apparent that such recycle of the aqueous phase will, in many instances, provide for recycle of at least a portion of the inhibitor originally charged to the reaction zone. The amount of said inhibitor being recycled to the reaction zone in the recycled aqueous phase can be conveniently determined by conventional analytical techniques. Allowance for the amount of isomerization inhibitor being recycled can then be made when charging additional inhibitor to the reaction zone.

Any amount of olefinic hydrocarbon, olefinically unsaturated mononitrile and monoadduct reaction product can be employed in the practice of this invention. In general the mol ratio of olefinically unsaturated mononitrile reactant to olefinic hydrocarbon reactant will be in the range of about 10:1 to about 0.1:1. Frequently the mol ratio of olefinically unsaturated mononitrile reactant to olefinic hydrocarbon reactant is in the range of about 5:1 to about 0.2:1; however, based upon the results of the runs hereinafter described it is believed that the ratio can be within the range of about 2:1 to about 0.3:1. In general the monoadduct reaction product is employed in an amount such that during substantially the entire reaction period the net monoadduct reaction product present in the reaction mixture will constitute from about 10 to about 90 weight percent of the total reaction mixture. Frequently the reaction is carried out such that the net monoadduct reaction product present in the reaction mixture is in the range from about 20 to about 80, and more often from about 30 to about 70 weight percent of the total reaction mixture. As used herein the term "net amount of monoadduct reaction product present in the reaction zone" is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it is generally preferred for them to be the same. The total reaction mixture includes all fluid materials present in the reaction zone, i.e. reactants, diluents, products, byproducts, etc.

Any suitable reaction conditions for either a batch process or a continuous process can be employed in the practice of the invention. The reaction time employed in the practice of this invention can vary widely. Generally a time period of from about two minutes to about 48 hours is used; however, a time period ranging from about 30 minutes to about 10 hours can also be used. The results of the runs herein indicate that the time period can be within the range of from about 1 hour to about 5 hours for the olefin, unsaturated mononitrile and the monoadduct reaction product to be suitably admixed in the preparation of reaction products in high yields in a batch process. In a continuous process the liquid hourly space velocity will generally be in the range of about 0.05 to about 20, preferably in the range of about 0.1 to about 10, more preferably in the range of about 0.5 to about 2.

The reaction temperatures that can be employed in the practice of the invention can be selected over a wide range. Generally, however, suitable reaction temperatures are within the range of from about 100° C. to about 500° C. On the basis of the results of the runs carried out it is believed that reaction temperatures within the range of from about 200° C. to about 350° C. can be employed.

The reaction pressures suited to the practice of this invention also vary widely. Reaction pressures within a range of from about atmospheric pressure to about 100,000 psig can be employed. On the basis of the results of the runs carried out it is believed that reaction pressures within the range of from about 500 psig to about 4000 psig can also be employed.

If desired, the processes of this invention can be carried out in the presence of a polymerization inhibitor. The use of the inhibitor often advantageously limits said reactions such as the dimerization or polymerization of the olefinically unsaturated mononitrile. When a polymerization inhibitor is employed, it is generally desirable that an amount within the range of from about 0.001 to about 5 percent by weight polymerization inhibitor based on the weight of unsaturated mononitrile reactant be employed; however, amounts ranging from about 0.1 to about 1 can also be employed based upon the runs carried out. A few examples of suitable inhibitors include hydroquinone, 2,6-di-tert-butyl-para-cresol, 2,6-di-tert-butylhydroquinone, 4-tert-butylcatechol, para-hydroxydiphenylamine, and the like, and combinations of any two or more thereof.

The reaction of the above-described olefinic hydrocarbon reactant, olefinically unsaturated mononitrile reactant and monoadduct reaction product reactant can be carried out in the presence of an aqueous diluent. Generally the aqueous diluent comprising at least 50 weight percent water, and more often at least 80 weight percent water. The reaction can be carried out employing an aqueous diluent consisting essentially of water if desired. A co-diluent can be employed if desired and can be any solvent or diluent which is nonreactive with either the reactants or the reaction products. Examples of suitable co-diluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and mixtures of any two or more thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. Based upon the results obtained employing 0.5 parts by weight of total diluent per part by weight olefinically unsaturated mononitrile reactant, the amount of diluent currently preferred is in the range of about 0.1 to about 20 parts by weight of total diluent per part by weight of olefinically unsaturated mononitrile reactant charged to the reaction zone. The advantages of the aqueous diluent system include improved selectivity to the desired olefinically unsaturated nitrile and reduced amounts of heavy polymeric byproduct. This latter byproduct is particularly objectionable because it tends to foul reactor surfaces.

A convenient method of carrying out this invention to produce a dinitrile comprises heating a mixture of an olefinically unsaturated mononitrile (e.g. acrylonitrile), an olefinic hydrocarbon compound (e.g. isobutylene), and a monoadduct reaction product reactant (e.g. a mixture of 5-methyl-5-hexenenitrile and 2,4-dimethyl-4-pentenenitrile) in a reaction pressure vessel at a temperature within the range of about 240° to about 350° C. and at pressures in the range of about 500 to about 4000 psig, the mol ratio of the olefinically unsaturated mononitrile to the olefinic hydrocarbon being in the range of about 5:1 to about 0.2:1, and the concentration of the monoadduct reaction product reactant in the reaction mixture being in the range of about 20 to about 80 weight percent. Thereafter, the resulting olefinically unsaturated dinitrile reaction product is readily isolated from the reaction effluent mixture by any convenient product recovery method, such as fractional distillation. The reaction can be carried out until the mononitrile reactant and/or the olefinic hydrocarbon reactant is depleted from the reaction media in apparatus well known to the art and suited to either batch or continuous reaction conditions.

If desired, the reaction can be carried out in the presence of any suitable promoter, for example an organo derivative of a Group VA element defined by the following formula $R^V_m ZH_{3-m}$ wherein each $R^V$ is independently selected from the group consisting of aryl, alkaryl, cycloalkylaryl, araryl, aryloxy, alkaryloxy, and arylaryloxy; wherein each $R^V$ group contains from 6 to 12 carbon atoms; Z is selected from the group consisting of N, P, P=O, As, Sb, or Bi; and m is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphospine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)-phosphine, triphenylphosphite, diphenyl(p-tolyl)phosphine, triphenylphosphate, and mixtures of any two or more thereof. The variant designated by n in mixtures of promoters represented by the formula $R^V_m ZH_{3-m}$ can vary, with the arithmetical sum of the value of m of individual promoters, from 2 to 3. The term "reaction promoting material" includes materials commonly called catalysts as well as materials commonly called promoters.

If employed, the amount of promoter utilized in the process of this invention can be selected over a wide range. In general, the mol ratio of promoter to unsaturated mononitrile reactant charged to the reaction zone is in the range of about 1:20 to about 1:1, although more often the mol ratio of promoter to unsaturated mononitrile reactant charge is in the range of about 1:10 to about 1:3.

The following examples are presented in further illustration of the invention but are not to be construed so as to unduly limit the invention.

EXAMPLE I

The three runs of this example are control runs for the instant invention. These runs were carried out by charging a 1 liter autoclave equipped with heating and stirring means with 70 grams of acrylonitrile, 315 grams of the monoadduct reaction product of acrylonitrile and isobutylene which had been previously prepared and recovered. In the first run no additives were added; in the second ammonia, a known isomerization inhibitor additive (not an isomerization inhibitor within the scope of the present invention) was introduced; and in the final run, 35 grams of water was added. The reactor was then flushed with nitrogen, charged with 160 grams of isobutylene and heated at 270° C. for 2.5 hours. The pressure employed was autogeneous and was about 2000 psig. The resulting reaction mixture was processed by fractional distillation and the recovered monoadduct analyzed by gas-liquid phase chromatography. A comparison of the gas-liquid phase chromatography (GLC) peak area percent for the undesired isomer (5-methyl-4-hexenenitrile) in the starting material (monoadduct) with the same GLC peak area percent in the recovered monoadduct provides a measure of the extent of isomerization of monoadduct that took place during the reaction period. The gas-liquid phase chromatography analyses were, of course, conducted under the same conditions in each instance. The results of these three runs are presented below in Table I.

Table I

| Run No. | H₂O Wt. % | Additive Type | Additive Wt. % | GLC Peak Area % Starting MA | GLC Peak Area % Product MA |
|---|---|---|---|---|---|
| 1 | 0 | none | — | 0.16 | 0.35 |
| 2 | 0 | ammonia | 1.6 | 0.16 | 0.28 |
| 3 | 50 | none | — | 0.16 | 0.90 |

[a]Based on weight of monoadduct charged (315 g.).
[b]GLC peak area percent determined for 5-methyl-4-hexenenitrile in monoadduct (MA).
[c]MA represents monoadduct.

Comparison of the results obtained in runs 1 and 3 demonstrate that although some isomerization to the undesired isomer occurs in the absence of water and isomerization inhibitor additive, the presence of water in the reaction mixture significantly promotes the formation of the undesired isomer in the absence of an isomerization inhibitor additive. Furthermore, in the absence of water, ammonia as an isomerization inhibitor additive, as shown in run 2, was only slightly effective under the conditions utilized in inhibiting the isomerization during the reaction period.

EXAMPLE II

A number of other runs were conducted in the same apparatus as previously described in Example I. The same amounts of acrylonitrile, monoadduct and isobutylene and the same techniques for measuring the extent of monoadduct isomerization during the reaction period were employed as in Example I. All of the runs in this example employed water as part of the reaction mixture in the amount of 50% by weight based on the weight of acrylonitrile charged to the reaction mixture. A variety of compounds were examined for their isomerization inhibitory effect under the conditions described. Included in this series of runs are several runs which are carried out according to the instant invention. Results of these runs are presented in Table II below. Run 3 of Example I, a control run, is also included in this tabulation for convenience in comparison with the results obtained in the other runs of the instant example. Run 6 of the instant example employed an isomerization inhibitor described in U.S. Pat. No. 4,001,294; however, the amount employed was somewhat less than the amount recommended in the patent.

TABLE II

| Run No. | Additive Type | Wt. %$^a$ | GLC Peak Area %$^b$ Starting MA | Product MA |
|---|---|---|---|---|
| 3 | none | — | 0.16 | 0.90 |
| 4 | Lithium acetate | 0.06 | 0.16 | 0.53 |
| 5 | Ammonia | 1.6 | 0.16 | 0.58 |
| 6 | EDTA$^c$ | 0.002 | 0.16 | 0.85 |
| 7 | Sodium methoxide | 0.11 | 0.16 | 0.58 |
| 8 | Lithium hydroxide | 0.22 | 0.16 | 0.53 |
| 9 | Sodium acetate | 0.31 | 0.16 | 0.42 |
| 10 | Potassium monohydrogen orthophosphate | 0.31 | 0.16 | 0.37 |
| 11 | Sodium carbonate | 0.22 | 0.16 | 0.43 |
| 12 | Potassium oxalate | 0.31 | 0.16 | 0.13 |
| 13 | Potassium hydrogen terephthalate | 0.31 | 0.16 | 0.28 |
| 14 | Potassium oxalate | 0.11 | 0.16 | 0.14 |
| 15 | Sodium citrate (tri-salt) | 0.22 | 0.16 | 0.23 |

$^a$Based on weight of monoadduct charged (315 g).
$^b$GLC peak area percent determined for 5-methyl-4-hexenenitrile in monoadduct (MA).
$^c$Trisodium salt of ethylenedinitrilo)tetraacetic acid.

Of all the runs presented in Table II, only those runs which employed potassium oxalate showed essentially complete inhibition of isomerization to the undesired isomer. All of the runs were better than the control run, run 3, which employed no additive, in the sense that the amount of isomerized monoadduct was less but, in each instance, the amount of undesirable monoadduct isomer in the recovered monoadduct was higher than in the starting monoadduct material. Runs 12 through 15 demonstrate the inhibiting effect of inhibitors of the present invention under the conditions employed. While the results of run 13 do not appear to be better than control run 2 in which ammonia was employed as the isomerization inhibitor, run 13 was carried out employing water in the reaction mixture and run 2 was carried out in the absence of water, a compound that clearly promotes isomerization to the undesired isomer as evidenced by run 3 described above. Runs 12 and 14 employing potassium oxalate provided the best results under the conditions employed.

EXAMPLE III

Another series of runs was carried out in essentially the same manner as that previously described in Examples I and II above and utilizing the same techniques for measuring the extent of monoadduct isomerization. In each run of the instant example, the diluent employed was water and the amount of water charged to the reaction mixture was 25 weight percent based on the amount of acrylonitrile charged. The runs of this example employed either potassium oxalate according to the instant invention or the trisodium salt of (ethylenedinitrilo)tetraacetic acid (EDTA). The latter compound is an isomerization inhibitor within the scope of those disclosed in U.S. Pat. No. 4,001,294. The results of these runs are presented in Table III below.

Table III

| Run No. | Additive Type | Wt. %$^a$ | GLC Peak Area %$^b$ Starting MA | Product MA |
|---|---|---|---|---|
| 16 | EDTA$^c$ | 0.002 | 0.16 | 0.37 |
| 17 | EDTA | 0.02 | 0.16 | 0.16 |
| 18 | EDTA | 0.01 | 0.16 | 0.20 |
| 19 | EDTA | 0.002 | 0.16 | 0.33 |
| 20 | EDTA | 0.006 | 0.16 | 0.23 |
| 21 | Potassium oxalate | 0.11 | 0.16 | 0.10 |
| 22 | Potassium oxalate | 0.006 | 0.16 | 0.10 |
| 23 | Potassium oxalate | 0.01 | 0.16 | 0.10 |
| 24 | Potassium oxalate | 0.0002 | 0.16 | 0.10 |

$^a$Based on weight of monoadduct charged (315 g).
$^b$GLC peak area percent determined for 5-methyl-4-hexenenitrile in monoadduct (MA).
$^c$Trisodium salt pf (ethylenedinitrilo)tetraacetic acid.

The results of Table III demonstrate again the high effectiveness of potassium oxalate as an isomerization inhibitor for the monoadduct. Furthermore, potassium oxalate is shown to be effective as an isomerization inhibitor at extremely low levels. Run 17 which utilized the prior art isomerization inhibitor additive, when compared with run 24 indicates that about 100 times as much of the prior art additive is required to achieve essentially no isomerization in the monoadduct.

That which is claimed is:

1. A method comprising:
   inhibiting the carbon-carbon double bond isomerization of a first compound having olefinic unsaturation in a less stable form to a second compound having olefinic unsaturation in a more stable form by contacting at least one alkali metal salt of a di-, tri-, or tetracarboxylic acid with said first compound in an amount sufficient to at least substantially inhibit the formation of said second compound, wherein said first compound is an acyclic or alicyclic olefinically unsaturated nitrile having 4 to 30 carbon atoms per molecule and having the —C≡N substituent attached to a carbon atom which is at least two carbon atoms, inclusive of the substituent-bearing carbon atom, removed from the nearest carbon atom of the olefinic double bond, and wherein said at least one alkali metal salt of a di-, tri-, or tetracarboxylic acid is represented by the general formula

$MO_2C—R(CO_2Z)_n$ wherein n is an integer having a value of 1, 2 or 3,
   wherein M is selected from the group consisting of lithium, sodium, potassium, rubidium and cesium, wherein each Z is independently selected from the group consisting of hydrogen, lithium, sodium, potassium, rubidium and cesium, and wherein R is selected from the group consisting of a valence bond, a hydrocarbyl radical having from 1 to 8 carbon atoms and having a valence equal to n+1, and a hydroxy substituted hydrocarbyl radical having from 1 to 8 carbon atoms and having a valence equal to n+1.

2. A method in accordance with claim 1 wherein the compound having olefinic unsaturation in a less stable form is a monoadduct selected from the group consisting of 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4methyl-4-pentenenitrile, 2(n-butyl)-4-pentenenitrile, 2-(n-butyl)-5-phenyl-4-pentenenitrile, and mixtures of any two or more thereof.

3. A method in accordance with claim 1 wherein the compound having olefinic unsaturation in a less stable form is 5-methyl-5-hexenenitrile which is produced by a reaction mixture comprising acrylonitrile and isobutylene in an aqueous diluent and the potassium salt of an aliphatic dicarboxylic acid.

4. The method of claim 3 wherein the potassium salt is potassium oxalate.

5. The method of claim 4 wherein the amount of potassium oxalate employed ranges from about 0.0001 to about 10 percent by weight based on the weight of said compound having olefinic unsaturation in said less stable form.

6. The method of claim 5 wherein the amount of potassium oxalate employed ranges from about 0.0002 to about 2 percent by weight based on the weight of said compound having olefinic unsaturation in said less stable form.

7. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, and at least one alkali metal salt of a di-, tri-, or tetracarboxylic acid represented by the general formula

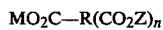

wherein n is an integer having a value of 1, 2 or 3,
wherein M is selected from the group consisting of lithium, sodium, potassium, rubidium and cesium,
wherein Z is selected from the group consisting of hydrogen, lithium, sodium, potassium, rubidium and cesium, and
wherein R is selected from the group consisting of a valence bond, a hydrocarbyl radical and a hydroxy substituted hydrocarbyl radical having from 1 to 8 carbon atoms and having a valence equal to n+1, under reaction conditions suitable to produce at least one olefinically unsaturated dinitrile product, wherein said monoadduct reaction product has olefinic unsaturation in a less stable form as compared to an isomeric form of said monoadduct reaction product having olefinic unsaturation in a more stable form, wherein each of said olefinically unsaturated mononitrile reactant and said olefinically unsaturated mononitrile compound contain at least one hydrogen atom attached to a doubly bonded carbon atom and contain a cyano group attached to a carbon atom adjacent and doubly bonded to a carbon atom which is attached to at least one hydrogen atom, wherein each of said olefinic hydrocarbon reactant and said olefinic hydrocarbon compound have at least one allylic hydrogen atom, wherein during substantially the entire reaction period the concentration of said monoadduct reaction product in the resulting reaction mixture is within the range of about 10 to about 90 weight percent of the total reaction mixture, and wherein the amount of said at least one alkali metal salt is an amount sufficient to at least substantially inhibit the carbon-carbon double bond isomerization of said monoadduct having olefinic unsaturation in the less stable form to produce an isomeric form of said monoadduct having olefinic unsaturation in a more stable form.

8. A process in accordance with claim 7 wherein the at least one alkali metal salt is selected from the group consisting of potassium oxalate, potassium malonate, potassium succinate, potassium glutarate, potassium adipate, potassium pimelate, potassium suberate, potassium azelate, potassium sebacate, potassium 2,3-dimethylbutanedioate, potassium 2-methylbutanedioate, potassium 2-methylpropanedioate, potassium 2-methylhexanedioate, potassium 2-ethyl-3-methylpentanedioate, potassium 3,3-dimethylpentanedioate, potassium 2,3-diethylbutanedioate, potassium hydrogen terephthalate, lithium hydrogen isophthalate, sodium hydrogen orthophthalate, potassium terephthalate, potassium isophthalate, sodium orthophthalate, sodium citrate, lithium oxalate, sodium oxalate, rubidium oxalate, cesium oxalate, sodium hydrogen oxalate, rubidium hydrogen oxalate, lithium malonate, sodium succinate, rubidium glutarate, cesium adipate, lithium pimelate, sodium suberate, rubidium azelate, cesium sebacate, lithium 2,3-dimethylbutanedioate, sodium 2-methylhexanedioate, rubidium 2-ethyl-2-methylpentanedioate, cesium 3,3-dimethylpentanedioate, lithium 2,3-diethylbutanedioate, sodium hydrogen adipate, potassium hydrogen pimelate, rubidium hydrogen suberate, cesium hydrogen azelate, lithium propane 1,2,3-tricarboxylate, potassium propane 1,2,3-tricarboxylate, potassium citrate, lithium citrate, sodium dihydrogen citrate, potassium dihydrogen citrate, sodium hydrogen citrate, potassium hydrogen citrate, sodium dihydrogen propane 1,2,3-tricarboxylate, potassium dihydrogen propane 1,2,3-tricarboxylate, sodium cyclopentane 1,2,3,4-tetracarboxylate, potassium cyclopentane 1,2,3,4-tetracarboxylate, cesium cyclopentane 1,2,3,4-tetracarboxylate, potassium trihydrogen cyclopentane 1,2,3,4-tetracarboxylate, potassium dihydrogen cyclopentane 1,2,3,4-tetracarboxylate, potassium hydrogen cyclopentane 1,2,3,4-tetracarboxylate and mixtures of any two or more such compounds.

9. A process in accordance with claim 7 wherein the at least one alkali metal salt is a potassium salt of a dicarboxylic acid.

10. A process in accordance with claim 7 wherein the at least one alkali metal salt is potassium oxalate.

11. A process in accordance with claim 7 wherein each of said at least one olefinic hydrocarbon reactant and said olefinic hydrocarbon compound is free of acetylenic unsaturation and has from 3 to 18 carbon atoms per molecule with from 1 to 2 nonconjugated carbon-carbon double bonds as the sole aliphatic unsaturation.

12. A process in accordance with claim 11 wherein each of said at least one olefinically unsaturated mononitrile reactant and said olefinically unsaturated mononitrile compound is free of acetylenic unsaturation, has from 1 to 2 nonconjugated carbon-carbon double bonds as the sole aliphatic unsaturation, and has from 3 to 18 carbon atoms per molecule.

13. A process in accordance with claim 12 wherein each of said at least one olefinic hydrocarbon reactant and said olefinic hydrocarbon compound is represented by the formula $R^{IV}{}_2C\!=\!CR^{IV}\!-\!CHR^{IV}{}_2$, wherein each $R^{IV}$ is independently selected from the group consisting of hydrogen and hydrocarbyl radicals; and wherein each of said at least one olefinically unsaturated mononitrile reactant and said olefinically unsaturated mononitrile compound is represented by the formula $R'''CH\!=\!CR'''\!-\!CN$ wherein each $R'''$ is independently selected from the group consisting of hydrogen and hydrocarbyl radicals.

14. A process in accordance with claim 13 wherein said reaction conditions comprise a temperature in the range of about 100° C. to about 500° C., a pressure in the range of about atmospheric to about 100,000 psig, the amount of the alkali metal salt employed ranges from about 0.0001 to about 10 percent by weight based on the weight of said compound having olefinic unsaturation in said less stable form, a mole ratio of said olefinically unsaturated mononitrile reactant to said olefinic hydrocarbon reactant in the range of about 10:1 to about 0.1:1, and carrying out the reaction in a diluent in an amount in the range of from about 0.01 to about 40 parts by weight per part by weight of said at least one olefinically unsaturated mononitrile reactant.

15. A process in accordance with claim 13 wherein said reaction conditions comprise a temperature in the range of about 240° C. to about 350° C., a pressure in the range of about 1000 to about 4000 psig, a contact time in the range of about 30 minutes to about 10 hours, the amount of the alkali metal salt employed ranges from about 0.0002 to about 2 percent by weight based on the weight of said compound having olefinic unsaturation in said less stable form, and a mole ratio of said olefinically unsaturated mononitrile reactant to said olefinic hydrocarbon reactant in the range of about 5:1 to about 0.2:1; and wherein said monoadduct reaction product having olefinic unsaturation in the less stable form is represented by the general formula:

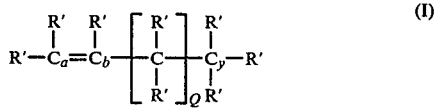 (I)

and the monoadduct reaction product having olefinic unsaturation in the more stable form is represented by the general formula:

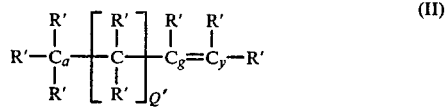 (II)

wherein R' is independently selected from the group consisting of hydrogen and an alkyl or a substituted alkyl radical having from 1 to 10 carbon atoms, wherein Q and Q' are the same or different and are within the range of from 0 to 7 and wherein the carbon atoms in the carbon-carbon double bond represented by $C_a\!=\!C_b$ in formula (I) have fewer alkyl or substituted alkyl radicals attached thereto as compared to the carbon atoms in the carbon-carbon double bond represented by $C_g\!=\!C_y$ in formula (II), and further comprising recovering from the resulting reaction effluent said at least one olefinically unsaturated dinitrile reaction product.

16. A process in accordance with claim 14 wherein said diluent consists essentially of water.

17. A process in accordance with claim 16 wherein during substantially the entire reaction period said concentration of monoadduct reaction product in said reaction mixture is maintained within the range of about 20 to about 80 weight percent.

18. A process in accordance with claim 17 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, wherein said olefinic hydrocarbon compound is isobutylene, and wherein said at least one alkali metal salt is potassium oxalate.

19. A process in accordance with claim 7 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

20. A process in accordance with claim 10 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

21. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound in the presence of an aqueous diluent, and at least one alkali metal salt of a di-, tri- or tetracarboxylic acid is represented by the general formula

wherein n is an integer having a value of 1, 2 or 3,
wherein M is selected from the group consisting of lithium, sodium, potassium, rubidium and cesium,
wherein Z is selected from the group consisting of hydrogen, lithium, sodium, potassium, rubidium and cesium, and
wherein R is selected from the group consisting of a valence bond, a hydrocarbyl radical and a hydroxy substituted hydrocarbyl radical having from 1 to 8 carbon atoms and having a valence equal to n+1, under reaction conditions suitable to produce at least one olefinically unsaturated dinitrile product, wherein said monoadduct reaction product has olefinic unsaturation in a less stable form as compared to an isomeric form of said monoadduct reaction product having olefinic unsaturation in a more stable form;
wherein each of said at least one olefinic hydrocarbon reactant and said olefinic hydrocarbon compound has from 3 to 18 carbon atoms and is represented by the formula $R^{IV}{}_2C\!=\!CR^{IV}\!-\!CHR^{IV}{}_2$, wherein each $R^{IV}$ is independently selected from the group consisting of hydrogen and hydrocarbyl radicals;

wherein each of said at least one olefinically unsaturated mononitrile reactant and said olefinically unsaturated mononitrile compound has from 3 to 18 carbon atoms and is represented by the formula $R'''CH=CR'''-CN$, wherein each $R'''$ is independently selected from the group consisting of hydrogen and hydrocarbyl radicals;

wherein the amount of said alkali metal salt is an amount sufficient to at least substantially inhibit the carbon-carbon double bond isomerization of said monoadduct having olefinic unsaturation in the less stable form to produce an isomeric form of said monoadduct having olefinic unsaturation in a more stable form;

wherein said at least one monoadduct reaction product having olefinic unsaturation in the less stable form is represented by the general formula:

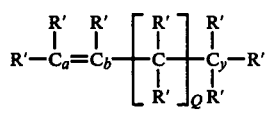 (I)

and the monoadduct reaction product having olefinic unsaturation in the more stable form is represented by the general formula:

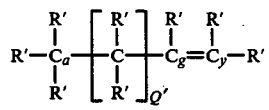 (II)

wherein $R'$ is independently selected from the group consisting of hydrogen and an alkyl or a substituted alkyl radical having from 1 to 10 carbon atoms, wherein Q and Q' are the same or different and are within the range of from 0 to 7 and wherein the carbon atoms in the carbon-carbon double bond represented by $C_a=C_b$ in formula (I) have fewer alkyl or substituted alkyl radicals attached thereto as compared to the carbon atoms in the carbon-carbon double bond represented by $C_g=C_y$ in formula (II);

wherein the amount of the said at least one alkali metal salt of a di-, tri- or tetracarboxylic acid employed ranges from about 0.0001 to about 10 percent by weight based on the weight of said compound having olefinic unsaturation in said less stable form;

wherein said at least one olefinically unsaturated dinitrile product is formed by the addition of one molecule of said olefinically unsaturated mononitrile reactant and one molecule of said monoadduct reaction product;

wherein said aqueous diluent comprises at least 50 weight percent water; the balance, if any, of said diluent being nonreactive with the reactants and the reaction products;

wherein the amount of said aqueous diluent is in the range of about 0.01 to about 40 parts by weight per part by weight of said at least one olefinically unsaturated mononitrile reactant;

wherein said reaction conditions comprise a temperature in the range of about 100° C. to about 500° C., a pressure in the range of about atmospheric to about 100,000 psig, and a reaction time in the range of about two minutes to about 48 hours for a batch process or a liquid hourly space velocity in the range of about 0.05 to about 20 for a continuous process;

wherein the mol ratio of said at least one olefinically unsaturated mononitrile reactant to said at least one olefinic hydrocarbon reactant is in the range of about 10:1 to about 0.1:1; and wherein during substantially the entire reaction period the concentration of said monoadduct reaction product in the resulting reaction mixture is within the range of about 10 to about 90 weight percent of the total reaction mixture.

22. A process in accordance with claim 21 wherein the at least one alkali metal salt is selected from the group consisting of potassium oxalate, potassium malonate, potassium succinate, potassium glutarate, potassium adipate, potassium pimelate, potassium suberate, potassium azelate, potassium sebacate, potassium 2,3-dimethylbutanedioate, potassium 2-methylbutanedioate, potassium 2-methylpropanedioate, potassium 2-methylhexanedioate, potassium 2-ethyl-3-methylpentanedioate, potassium 3,3-dimethylpentanedioate, potassium 2,3-diethylbutanedioate, potassium hydrogen terephthalate, lithium hydrogen isophthalate, sodium hydrogen orthophthalate, potassium terephthalate, potassium isophthalate, sodium orthophthalate, sodium citrate, lithium oxalate, sodium oxalate, rubidium oxalate, cesium oxalate, sodium hydrogen oxalate, rubidium hydrogen oxalate, lithium malonate, sodium succinate, rubidium glutarate, cesium adipate, lithium pimelate, sodium suberate, rubidium azelate, cesium sebacate, lithium 2,3-dimethylbutanedioate, sodium 2-methylhexanedioate, rubidium 2-ethyl-2-methylpentanedioate, cesium 3,3-dimethylpentanedioate, lithium 2,3-diethylbutanedioate, sodium hydrogen adipate, potassium hydrogen pimelate, rubidium hydrogen suberate, cesium hydrogen azelate, lithium propane 1,2,3-tricarboxylate, potassium propane 1,2,3-tricarboxylate, potassium citrate, lithium citrate, sodium dihydrogen citrate, potassium dihydrogen citrate, sodium hydrogen citrate, potassium hydrogen citrate, sodium dihydrogen propane 1,2,3-tricarboxylate, potassium dihydrogen propane 1,2,3-tricarboxylate, sodium cyclopentane 1,2,3,4-tetracarboxylate, potassium cyclopentane 1,2,3,4-tetracarboxylate, cesium cyclopentane 1,2,3,4-tetracarboxylate, potassium trihydrogen cyclopentane 1,2,3,4-tetracarboxylate, potassium dihydrogen cyclopentane 1,2,3,4-tetracarboxylate, potassium hydrogen cyclopentane 1,2,3,4-tetracarboxylate and mixtures of any two or more such compounds.

23. A process in accordance with claim 21 wherein the at least one alkali metal salt is a potassium salt of a dicarboxylic acid.

24. The process in accordance with claim 21 wherein the at least one alkali metal salt is potassium oxalate.

25. A process in accordance with claim 21 wherein said diluent comprises at least 80 weight percent water and wherein the amount of the alkali metal salt employed ranges from about 0.0002 to about 2 percent by weight based on the weight of said compound having olefinic unsaturation in said less stable form.

26. A process in accordance with claim 24 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

27. A process in accordance with claim 26 wherein said diluent consists essentially of water.

28. A process in accordance with claim 27 further comprising recovering from the resulting reaction effluent said at least one olefinically unsaturated dinitrile reaction product.

29. A process in accordance with claim 21 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

* * * * *